United States Patent [19]
Gee et al.

[11] Patent Number: 5,888,829
[45] Date of Patent: Mar. 30, 1999

[54] PHOTOLABILE CAGED IONOPHORES AND METHOD OF USING IN A MEMBRANE SEPARATION PROCESS

[75] Inventors: Kyle R. Gee, Springfield; Paul J. Millard, Eugene, both of Oreg.

[73] Assignee: Molecular Probes, Inc., Eugene, Oreg.

[21] Appl. No.: 638,261

[22] Filed: Apr. 26, 1996

Related U.S. Application Data

[63] Continuation-in-part of Ser. No. 336,284, Nov. 8, 1994, Pat. No. 5,635,608.

[51] Int. Cl.⁶ .................... G01N 21/00; G01N 33/558; C07H 1/06

[52] U.S. Cl. ................ 436/164; 210/649; 436/514; 536/1.11

[58] Field of Search .................. 210/321.6, 638, 210/643, 644, 649, 650, 651; 436/514, 164, 172; 422/82.05–82.08, 101; 536/1.11

[56] References Cited

U.S. PATENT DOCUMENTS

| | | |
|---|---|---|
| 4,849,362 | 7/1989 | DeMarinis et al. . |
| 4,981,985 | 1/1991 | Kaplan et al. . |
| 5,134,232 | 7/1992 | Tsien et al. . |
| 5,141,627 | 8/1992 | Tsien et al. . |
| 5,405,975 | 4/1995 | Kuhn et al. . |
| 5,453,517 | 9/1995 | Kuhn et al. . |
| 5,501,980 | 3/1996 | Katerinopoulos et al. . |
| 5,525,232 | 6/1996 | Veiro et al. ............... 210/643 |
| 5,635,608 | 6/1997 | Haugland et al. ........... 536/1.1 |

OTHER PUBLICATIONS

Ramesh, et al., Proc. Nat. Acad. Sci. 90, 11074 (1993).
Haugland, Molecular Probes Handbook of Fluorescent Probes and Research Chemicals, Sets 20–23 and 25 (1992–94).

*Primary Examiner*—Joseph W. Drodge
*Attorney, Agent, or Firm*—Allegra J. Helfenstein; Anton E. Skaugset

[57] ABSTRACT

The present invention describes a family of photolabile caged ionophores. The compounds of the present invention are photolytically cleavable esters of nigericin, ionomycin, A-23187, 4-Br-A-23187 and monensin. The photolysis of the present compounds allows the release of the free ionophore in vivo or in vitro with precise spatial and temporal control. The compounds are useful in the study of ion transport and control in cells and across membranes.

20 Claims, 2 Drawing Sheets

PHOTOLABILE CAGED IONOPHORES AND METHOD OF USING IN A MEMBRANE SEPARATION PROCESS

This application is a continuation-in-part of application Ser. No. 08/336,284, filed Nov. 08, 1994, now U.S. Pat. No. 5,635,608.

FIELD OF THE INVENTION

The present invention describes a family of photolabile caged ionophores. The compounds of the present invention are caged analogs and derivatives of the ionophores nigericin, ionomycin, A-23187, 4-bromo A-23187 and monensin. The present compounds are useful for the precise regulation of ion transport in living cells. In particular, the photolysis of the present compounds within cells can be used to initiate proton or metal cation transport with precise spatial and temporal control.

BACKGROUND

Covalent attachment of a photoremoveable group to a parent compound (i.e. "caging") to alter its physical or biological properties has been exploited extensively for following components of dynamic systems. As used herein, the term "cage" refers to a photolytically sensitive substituent that is designed to interfere with the reactivity or other physical properties of the free probe. Photolysis (typically by illumination in the UV (250–400 nm) region of the spectrum) cleaves the caging group from the parent compound, restoring its normal properties. In this way it is possible to release the parent compound into the system of interest with much better temporal and spatial resolution than is possible by simple diffusion.

Appropriate caging groups for compounds used in the study of processes that change rapidly, such as biological processes, must be photolyzed rapidly and with relatively high quantum yield. It is also important that caging alters some property of the parent compound to the desired level, and that the caged compound remains useful in the system of interest. A variety of caged probes exist. For example, the o-nitrobenzyl group has been used to cage the calcium ion mobilizer 1,4,5-inositol triphosphate ($IP_3$). However, $IP_3$ acts by mobilizing intracellular calcium stores, and does not itself transport calcium ions.

Calcium ion levels in cells have been manipulated using other caged probes. Both diazo-2 and caged EGTA have been used to alter physiological calcium levels in cells. Nitrophenyl EGTA is a photolabile $Ca^{2+}$ chelator that exhibits an ~12,500-fold decrease in binding affinity upon photolysis. Therefore, upon illumination of nitrophenyl-EGTA, the calcium ions bound to the chelator are released, increasing cytoplasmic $Ca^{2+}$ levels (U.S. Pat. No. 5,446,186 to Ellis-Davies et al. (1995)). Similarly, 4,5-dimethoxy-2-nitrophenyl EDTA (sold under the trademark DM-NITROPHEN) releases calcium ions upon illumination (U.S. Pat. No. 4,981,985 to Kaplan et al. (1991)). In contrast, diazo-2 is a photolabile calcium indicator whose affinity for $Ca^{2+}$ increases approximately 30-fold upon illumination. Diazo-2 has been used to rapidly decrease cytoplasmic $Ca^{2+}$ levels in tensed frog muscle cells and in rat fibroblasts (Diazo-2 is described in U.S. Pat. No. 5,141,627 to Tsien et al. (1992)). While these caged probes are useful for manipulating intracellular calcium ion levels, they function by physically depleting or introducing the ions themselves from within the intracellular milieu. The caged probes of the present invention, in contrast, function by actively shuttling ions across cell membranes or other semi-permeable barriers after photolysis of the caging group.

The present invention describes caged ionophores that can be used to study the physiological effects of the free ionophore in sample systems, including cells. The use of a caged ionophore allows the free ionophore to be produced within the sample with precise control, both temporally and spatially. By using focused laser illumination, the free ionophore can be generated at specific locations within a single cell or within a tissue, within the limits of the ability to focus the photolytic illumination.

SUMMARY OF THE INVENTION

The present invention comprises a family of caged ionophores, including proton-, calcium ion-, and magnesium ion-transport regulators. The compounds of the present invention are utilized to initiate ion transport across semipermeable membranes with precise control both temporally and spatially. The present invention further comprises a method of modulating an ion concentration across a membrane that separates unequal ion concentrations.

DESCRIPTION OF THE PREFERRED EMBODIMENTS

Figure 1:
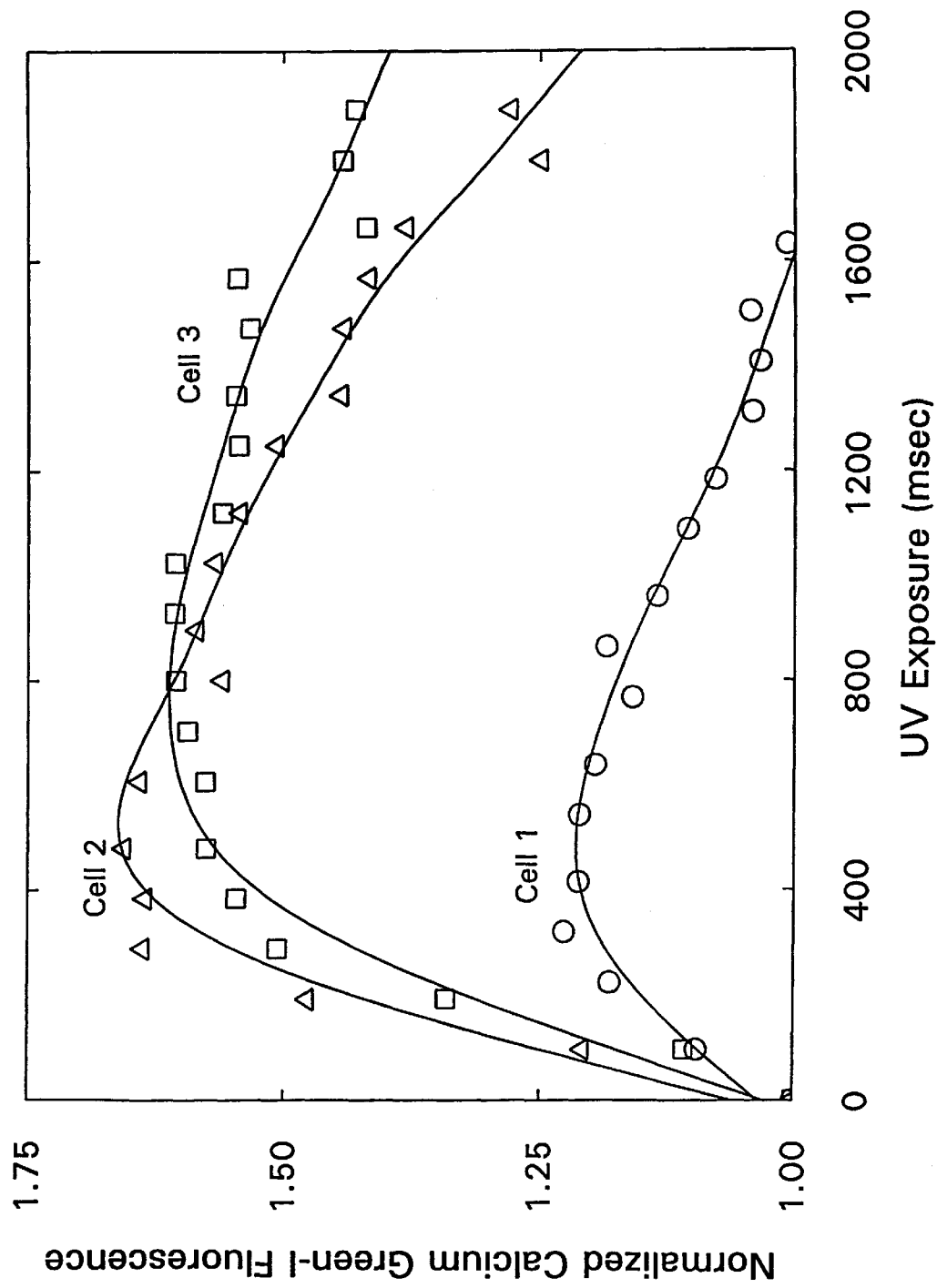
FIG. 1. Normalized fluorescence of CALCIUM GREEN-1 indicator in three individual 3T3 cells during the course of exposure to UV light in the presence of 10 $\mu$M caged-A-23187 (Compound 1), as described in Example 9.

The compounds of the present invention are ionophores, or molecules that act as ion-transport agents, that have been "caged" by a photolabile caging group on a carboxyl group that is intrinsically present on the ionophore molecule. By photolabile caging group is meant a chemical moiety that, when bound to the ionophore, prevents or reduces the biological activity of the ionophore. Further, the photolabile caging group of the invention, upon illumination, releases the free ionophore. In the present invention, both the caging group and the specific carboxylic acid moiety to be caged are selected so as to interfere with the ability of the ionophore to act as an ion-transport agent. Preferably, the caging group is selected so as to maximally interfere with the ability of the ionophore to act as an ion-transport agent.

Ionophores

In one embodiment of the invention, the ionophore that is caged is nigericin, ionomycin. A-23187 (also called calcimycin), 4-bromo-A-23187 or monensin. The ionophores of the invention, upon photolysis of the caging group, act as ion-transport agents, and equilibrate ion gradients across membranes. Typically, the ionophore is capable of transporting protons, monovalent or divalent metal cations.

Nigericin is an ionophore for protons and alkali metal ions. Free nigericin is capable of equalizing pH gradients across membranes, as well as transporting monovalent cations such as $Na^+$ or $K^+$. The structure of caged nigericin is:

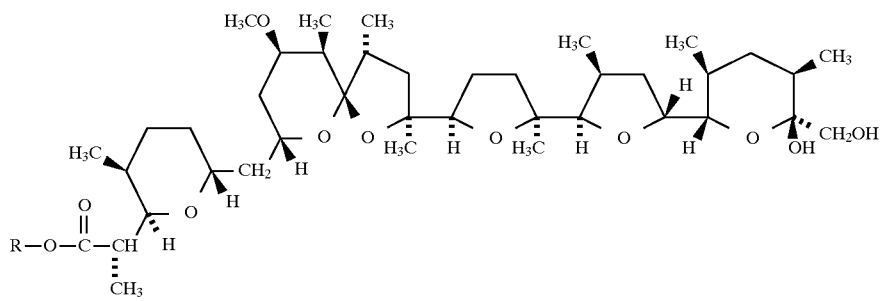

where R is the photolabile caging group.

Ionomycin is an ionophore for divalent metal cations, particularly $Ca^{2+}$ and $Mg^{2+}$. The structure of caged ionomycin is:

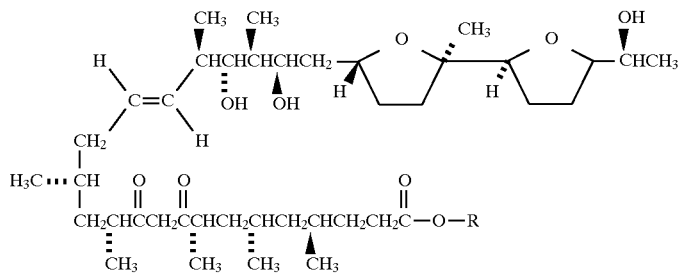

where R is the photolabile caging group.

A-23187 is also known as the ionophore calcimycin. A-23187 is an ionophore capable of transporting a variety of cationic metal ions with the following selectivity: $Mn^{2+} > Ca^{2+} > Mg^{2+} > Ba^{2+} > Li^+ > Na^+ > K^+$. The structure of caged A-23187 is:

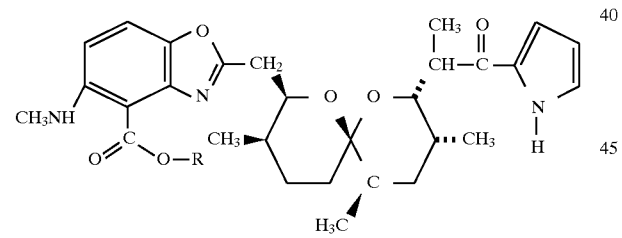

where R is the photolabile caging group.

4-Br-A-23187 is the 4-bromo analog of A-23187, and possesses substantially similar ion-transport properties as the parent ionophore. The structure of caged 4-Br-A-23187 is:

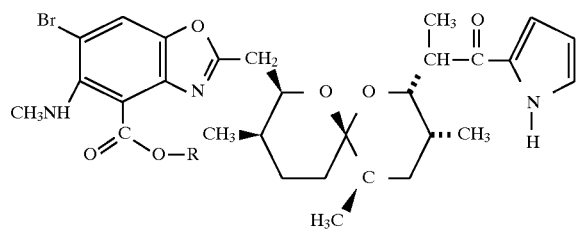

where R is the photolabile caging group.

Monensin is an ionophore for monovalent cations, typically $Na^+$ ions. The structure of caged monensin is:

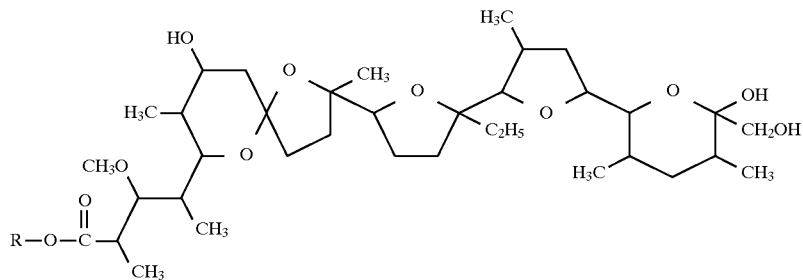

where R is the photolabile caging group.

Each ionophore is caged on a free carboxylic acid, as described below.

With the exception of A-23187, each of the ionophores of the present invention is non-fluorescent, and therefore fully suitable for use in the presence of fluorescent reagents, such as calibrated fluorescent pH or metal ion indicators. The ionophore A-23187 possesses intrinsic blue fluorescence (emission max. in MeOH=435 nm) that may interfere with the use of selected fluorescent reagents. However, it was found that caging the ionophore A-23187 unexpectedly renders it essentially non-fluorescent. Upon photolysis, the fluorescence of the free ionophore is restored (as described in Example 1). The use of caged A-23187 therefore provides an opportunity to easily verify that the free ionophore is being produced by simply monitoring the appearance of A-23187 fluorescence in the sample upon photolytic illumination.

In one embodiment of the invention, the caged ionophore is a caged nigericin, ionomycin, A-23187, 4-bromo-A-23187 or monensin. In another embodiment of the invention, the caged ionophore is a caged nigericin, ionomycin, A-23187 or 4-bromo-A-23187. In yet another embodiment of the invention, the ionophore that is caged is A-23187 or 4-Br-A-23187.

Caging Groups

Any group that blocks binding of the ion of interest to the ionophore through formation of an ester of the carboxylic acid and that can be photolytically removed by exposure to illumination is useful as a caging group. Typically, the caging group is selected so that it can be photolytically removed by ultraviolet illumination at a wavelength longer than 250 nm, preferably longer than 300 nm. Preferred caging groups are those that have absorption at some wavelengths between 300–400 nm. Additionally preferred caging groups possess photolysis quantum yields of greater than 0.05, preferably greater than 0.1, and that can be photolyzed with first order kinetic rates of 1/sec or faster, preferably on the order of $10^3$/sec. Preferred caged groups, upon photolysis, generate photolysis products that are not toxic to cells. Several such caging groups are known that are aryl or aryl alkyl esters (commonly benzyl esters). Especially preferred are substituted or unsubstituted nitrobenzyl esters (usually o-nitrobenzyl esters), m-nitroaryl esters (especially 2-alkoxy-5-nitrophenyl esters) and desyl esters.

In one embodiment of the invention, the photolabile caging group is a o-nitroarylmethine, for example:

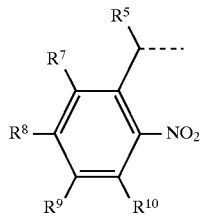

where $R^5$ is one of H, $CH_3$, or $CO_2R^6$, where $R^6$ is H, $C_{1-6}$ alkyl, an alpha-acyloxyalkyl ester having 3–6 carbons, an alkali metal, or a succinimide (such that $CO_2R^6$ is a succinimidyl ester). $R^7$, $R^8$, $R^9$ and $R^{10}$ are independently H, alkoxy having 1–6 carbons, —O(CH$_2$)$_n$CO$_2$R$^{11}$ (where n=1–18 and $R^{11}$ is H, alkyl having 1–6 carbons, or a succinimide (such that $CO_2R^{11}$ is a succinimidyl ester)) or $R^8$ taken in combination with $R^9$ is methylenedioxy (—O—CH$_2$—O—), or $R^7$ is NO$_2$. Caging moieties that are alphacarboxy nitroarylmethines (compounds wherein $R^5$ is $CO_2R^6$) have been previously described in U.S. Pat. No. 5,635,608 to Haugland, filed Nov. 8, 1994 (incorporated by reference). Where $R^6$ is an alkali metal ion, the effect of the addition of alkali metal ions to the sample should be considered when evaluating the response of the sample to the ionophore. In particular, $R^6$ should be selected so as not to disturb the concentration of the ion of interest in the sample. In one embodiment of the invention, $R^5$ is $CH_3$ or $CO_2R_6$ where $R^6$ is H or an alkali metal. In another embodiment of the invention, $R^8$ and $R^9$ are each methoxy or taken in combination are methylenedioxy. In yet another embodiment of the invention, $R^7$ is H or $NO_2$.

In another embodiment of the invention, the photolabile caging group is a 2-alkoxy-5-nitrophenyl, e.g.:

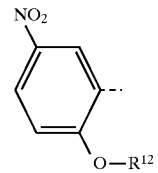

where $R^{12}$ is a $C_1$–$C_6$ alkyl (typically methyl), and the phenyl portion of the caging group is optionally substituted one or more times by halogen or methylenedioxy.

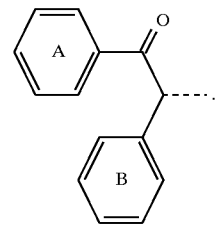

In another embodiment of the invention, the photolabile caging group is a desyl group, e.g.:

Aromatic rings A and B are optionally and independently substituted one or more times by H, halogen, —NO$_2$, —OR$^{13}$, and —NR$^{14}$R$^{15}$ where $R^{13}$, $R^{14}$ and $R^{15}$ are independently alkyl groups having 1–6 carbons. Preferably, where aromatic rings A and B are optionally substituted, they are substituted one or more times by —OR$^{13}$ or —NR$^{14}$R$^{15}$. Preferably there are no more than two non-hydrogen substituents on each of rings A and B. Where the caging group is additionally utilized to quench the fluorescence of the ionophore A-23187, at least one of aromatic rings A and B is substituted at least once by —NO$_2$.

Synthesis of materials

Nitrobenzyl Ester Caging Procedure

The attachment of a caging group to the carboxylic acid group of the ionophore is straightforward. In one embodiment, a solution of the ionophore is treated with an excess of diazabicyclo[5.4.0]undec-7-ene (DBU) and a 2-nitrobenzyl bromide to give the caged carboxylic acid after evaporation and purification of the residue via normal phase flash chromatography (Example 5). Alternatively, a solution of the ionophore is treated with a solution of a 1-(2-nitrophenyl)diazoalkane to give the caged carboxylate ester after concentration and purification of the residue via normal phase flash chromatography (Examples 1–3). In an alternate strategy, a solution of the ionophore is treated with a solution of a t-butyl 2-bromo-2-(2-nitrophenyl)acetate and DBU. After the reaction is complete, with heating as necessary, the intermediate is purified by filtration and chromatography of the concentrated filtrate residue. In this case, the intermediate is converted to the final product by treatment with trifluoroacetic acid in dichloromethane after concentration and purification of the residue via normal phase flash chromatography (Example 8).

Desyl Caging Procedure

A desyl caging group is attached to the carboxylic acid of the ionophores of the present invention by treating a solution of the ionophore with a solution of a desyl bromide and DBU. After heating (if necessary), the DBU-hydrobromide side product is removed by filtration and the product is purified by normal phase chromatography (as described in Example 6).

o-Alkoxy-p-Nitroalkyl Ester Caging Procedure

The carboxylic acid of the free ionophore is coupled to a substituted or unsubstituted 2-alkoxy-5-nitrophenol using 1-ethyl-3-(3-dimethylaminopropyl)-carbodiimide hydrochloride (EDAC) (Ramesh et al. PROC. NAT. ACAD. SCI. 90, 11074 (1993)), using 1-hydroxybenzotriazole hydrate (HOBT) and 4-dimethylaminopyridine (DMAP) to catalyze the esterification. After the reaction solution is washed with weak base and weak acid and then concentrated, the product is isolated by normal phase chromatography (as described in Example 7).

Sample Types

The caged ionophores of the present invention are useful for analyzing the responses of a sample component to the free ionophore under study. Typically, the sample comprises a lipid bilayer, either natural or synthetic, that is an impermeable or semi-permeable membrane across which exists a pH gradient or concentration gradient of the metal ion of interest. The membrane optionally contains protein constituents. In one embodiment, the membrane is an artificial lipid bilayer, such as a black lipid membrane, or such as occurs in an artificial liposome. In an additional embodiment, the membrane is a cell membrane, and the sample contains one or more cells. Where the sample comprises cells, the cells present in the sample are optionally plant cells, animal cells or unicellular organisms such as bacteria or yeast cells. The animal cells are optionally invertebrate, amphibian, or mammalian cells. In one embodiment of the invention, the cells of the sample are mammalian cells.

Method of use

In one aspect of the invention, the caged ionophores are used to control the modulation of an ion concentration across a membrane that separates unequal concentrations of that ion. The caged ionophore is placed in the presence of a membrane across which is an unequal ion concentration. Preferably the caged ionophore is added to the sample by passive loading. Typically, where the probe is not intrinsically water soluble, it is first dissolved in a water miscible solvent such as dimethylsulfoxide (DMSO) to facilitate its dispersion in the sample. The caged ionophore probes of the invention are typically lipophilic enough to equilibrate the probe within the membrane of interest without requiring disruption of that membrane. Where the membrane is a cell membrane, the ionophores of the invention typically bind to the cells without significant disruption of the cell membrane, when added to the sample by passive loading.

To facilitate access to an intracellular membrane, the caged ionophore of the present invention may be substituted by an alpha-acyloxyalkyl ester, and the ester is readily cleaved in cells by intracellular esterases. Alternatively, the caged ionophore is introduced into cells by pressure microinjection, scrape loading techniques (short mechanical disruption of the plasma membrane where the plasma membrane is peeled away from the cytoplasm, the caged ionophore is perfused through the sample and the plasma membrane is reassembled), patch clamp methods (where an opening is maintained in the plasma membrane for long periods) or phagocytosis to facilitate access to intracellular membranes. Any other treatment that will temporarily permeabilize the plasma membrane, such as electroporation or high extracellular ATP, can be used to introduce the caged ionophore into the cellular cytoplasm, provided that sufficient time is allowed after the membrane permeabilization for the sample to reequilibrate before the caged ionophore is photolyzed.

Illumination

After combination with the desired sample, the caged probes of the present invention are photolyzed to cleave the caging group and produce a free ionophore. The caged probe is optionally photolyzed at any wavelength at which that caged probe absorbs light. Typically, the caged probe is illuminated with ultraviolet light. This photolytic illumination typically has a wavelength longer than 200 nm, preferably longer than 250 nm, more preferably longer than 300 nm. Although the photolytic illumination typically has a wavelength greater than 200 nm, in order to prevent damage to biological systems (when present) the illumination preferably has a wavelength greater than 300 nm. In one embodiment of the invention, the caged probe is illuminated at a wavelength of 300–400 nm. In another embodiment of the invention, the caged probe is illuminated at a wavelength of 300–370 nm.

The photolytic illumination of compounds of the present invention is completely analogous to photolysis procedures known in the art for other caged probes, and is well known to one of ordinary skill. Illumination of the caged compound within the absorption bands of the photolabile caging group is required, typically using a light source capable of radiation at less than about 400 nm. Light sources having substantially longer wavelength may be used where the caged ionophore is being photolyzed using multiple-photon techniques (such as 2- or 3-photon excitation). Typical light sources include mercury arc lamps, flash lamps and lasers such as nitrogen lasers. As analyzed by thin layer chromatography, the caged compounds of the invention are efficiently photolyzed to the free agent even by a hand-held UV lamp. The photolytic illumination is typically generated using an ultraviolet laser. Photolysis of a solution of a compound of the present invention typically produces a mixture of caged and free ionophores. The photolysis rates and quantum yields are readily calculated for any probe according to known means that have been described for other probes.

Measurement

The determination of the response of the biological sample to the free ionophore after uncaging will depend upon the nature of the ionophore, and the nature of the sample. As cellular ion-transport affects and is effected by many cellular processes and enzymatic pathways, the caged probes of the present invention offer opportunities to study ion-transport in a variety of systems. A variety of reagents and methods are well-known in the art for detecting and quantifying ion concentrations in sample systems. The effect of ion-transport by the free ionophore is optionally monitored using calorimetric, fluorescent or luminescent indicators; through the use of ion-selective electrodes; or by observing a known response of the system that has been found to be coupled to ion-transport, such as enzymatic activity or electrical activity.

Where the ions being transported within the sample are protons, the ion transport is optionally observed directly by the use of a fluorescent or calorimetric pH indicator. Suitable pH indicators for the purpose of this invention include, but are not limited to, SNAFL indicators, SNARF indicators, rhodol indicators, Cl-NERF indicators or derivatives of BCECF (all of which are available from Molecular Probes, Inc., Eugene OR). In addition, lipophilic versions of these indicators, or dextran conjugates of these indicators typically possess utility in cellular applications.

Where the ions being transported are monovalent metal ions, particularly $Na^+$ or $K^+$ ions, such transport is optionally observed directly by the use of a fluorescent or calorimetric ion indicator. Suitable $Na^+$ and $K^+$ indicators for the purposes of this invention include, but are not limited to, those described in U.S. Pat. No. 5,134,232 to Tsien et al. (1992), sold under the names SBFO, SBFI and PBFI (available from Molecular Probes, Inc., Eugene Oreg.). Also suitable are the sodium indicators described in U.S. Pat. No. 5,405,975 to Kuhn et al., (1995), sold under the trademark SODIUM GREEN (Molecular Probes, Inc., Eugene Oreg.).

Where the ions being transported are divalent metal ions, particularly $Ca^{2+}$ or $Mg^{2+}$ ions, such transport is optionally observed directly by the use of a fluorescent or colorimetric calcium or magnesium ion indicator (as demonstrated in Example 9). Suitable calcium indicators for the purposes of this invention include, but are not limited to Fluo-3 (Example 10), Fura-2, or Indo-1 (available from Molecular Probes, Inc., Eugene Oreg.). Also suitable are the calcium indicators described in U.S. Pat. No. 5,453,517 to Kuhn et al. (1995). Selected embodiments of these indicators are sold under the trademarks CALCIUM GREEN, CALCIUM ORANGE and CALCIUM CRIMSON (Molecular Probes, Inc., Eugene Oreg.). Also suitable are the long-wavelength calcium indicators described in U.S. Pat. No. 5,501,980 to Katerinopoulos et al. (1996). A specific embodiment of these indicators is sold under the name BTC (Molecular Probes, Inc., Eugene Oreg.). An additional useful fluorescent calcium indicator has been described in U.S. Pat. No. 4,849,362 to DeMarinis et al. (1989) and is sold under the trademark FURA RED (Molecular Probes, Inc., Eugene Oreg.); and calcium ion indicators with enhanced photostability sold under the trademark OREGON GREEN BAPTA indicators (Molecular Probes, Inc., Eugene, Oreg.).

A variety of indicators for metal ions, pH indicators, ion probes and assays for selected cellular functions are described by Haugland, MOLECULAR PROBES HANDBOOK OF FLUORESCENT PROBES AND RESEARCH CHEMICALS Sets 20–23 and 25 (1992–94).

The examples below are given so as to illustrate the practice of this invention. They are not intended to limit or define the entire scope of this invention.

EXAMPLES

Example 1

Preparation of A-23187, 1-(4,5-dimethoxy-2-nitrophenyl)ethyl ester (Compound 1)

To a pale yellow solution of 4,5-dimethoxy-2-nitroacetophenone hydrazone (18 mg, 0.075 mmol) in chloroform (1.5 mL) is added manganese dioxide (70 mg, 0.81 mmol). The resulting mixture is stirred for 15 minutes in darkness, then filtered through diatomaceous earth with chloroform rinse (2×1 mL). To the combined red-orange diazoethane filtrate is added a solution of the ionophore A-23187 (26.9 mg, 0.0514 mmol, Sigma) in 1.5 mL chloroform. After stirring overnight, the color of the reaction solution is pale yellow and TLC analysis shows no remaining free A-23187. The reaction solution is diluted with chloroform (5 mL), and glacial acetic acid (5 drops) is added to quench any remaining diazoalkane. Concentration of the solution under vacuum gives a pale yellow oil, which is then purified by flash chromatography on silica gel using 5% methanol/chloroform as eluant. Compound 1 is obtained as 37 mg (97%) of a pale yellow microcrystalline solid. On TLC the two product diastereomers are resolved using chloroform/methanol/acetic acid (100:5:1) as eluant, giving two spots at $R_f$=0.36 and 0.43, respectively. These spots are initially quenching, but become fluorescent blue upon illumination with a hand-held UV lamp (unmodified A-23187 has an $R_f$=0.21). Two-dimensional TLC experiments show that after 10 minutes irradiation at 366 nm with a hand-held UV lamp, both diastereomers of the title compound are cleanly photolyzed into native A-23187. For Compound 1: m.p. 108°–116° C. (dec); $^1$H NMR (CDCl$_3$) δ=9.6, 9.3 (two br s, 1H), 8.2, 8.0 (two 2, 1H), 7.6 (m, 3H), 6.9 (m, 2H), 6.6 (t, 1H), 6.25 (dq, 1H), 4.2–2.8 (m, 13H), 1.8–0.7 (m, 26H). HPLC analysis shows the presence of both product diastereomers, in 93% purity.

Example 2

Preparation of 4-bromo-A-23187, 1-(4,5-dimethoxy-2-nitrophenyl)ethyl ester (Compound 2)

The diazoethane intermediate is formed as described in Example 1, using 36 mg (0.15 mmol) of the hydrazone and 0.13 g (1.5 mmol) manganese dioxide. To a solution of this intermediate in chloroform (2 mL) is added a solution of 4-bromo-A-23187 (76 mg, 0.13 mmol) in chloroform (2 mL) over five minutes. After 45 minutes, TLC shows product formation and the starting ionophore to be consumed. After the volatiles are removed under vacuum, the residue is purified by flash chromatography to give the title compound as 80 mg (79%) of a pale yellow microcrystalline solid. Photolysis with a hand-held UV lamp shows that the resulting product ($R_f$=0.76, 5% MeOH/CHCl$_3$) is photolyzed cleanly into free 4-bromo-A-23187 ($R_f$=0.10, 5% MeOH/CHCl$_3$). For Compound 2: $^1$H NMR (CDCl$_3$) δ=9.5, 9.3 (two br s, 1H), 8.0–7.5 (six s, 3H), 7.0–6.8 (m, 3H), 6.2 (q, 1H), 4.1–2.8 (m, 13H), 1.8–0.7 (m, 26H).

Example 3

Preparation of nigericin, 1-(4,5-dimethoxy-2-nitrophenyl)ethyl ester (Compound 3)

The diazoethane intermediate is formed as described in Example 1, using 55 mg (0.23 mmol) of the hydrazone and 0.16 g (1.8 mmol) manganese dioxide. To a solution of this intermediate in chloroform (2 mL) is added a solution of nigericin (75 mg, 0.10 mmol) in chloroform (2 mL) over five minutes. The resulting red-orange solution is stirred overnight, during which the color fades to pale yellow. The volatiles are removed in vacuo, and the residue purified by flash chromatography using MeOH/CHCl$_3$ (0% to 2%) as eluant. Compound 3 is obtained as 97 mg (98%) of a pale yellow-orange solid. TLC using 5% MeOH/CHCl$_3$ as eluant separates the two product diastereomers ($R_f$=0.28, 0.36, respectively). Photolysis with a hand-held UV lamp generates free nigericin ($R_f$=0.12, 5% MeOH/CHCl$_3$) as determined by TLC analysis. For the title compound: $^1$H NMR (CDCl$_3$) δ=7.7, 7.6 (4 s, 1H), 7.1, 6.9 (m, 1H), 5.4 (s, 1H), 4.8 (s, 1H), 4.4–3.1 (m, 19H), 2.5–0.8 (m, 38H).

Example 4

Preparation of A-23187, 1-(2-nitrophenyl)ethyl ester (Compound 4)

To a pale yellow solution of 2-nitroacetophenone hydrazone (Walker et al., J. Am. Chem. Soc. 1988, 110, 7170–7177) in chloroform is added 5 molar equivalents of manganese dioxide. The resulting mixture is stirred for 15 minutes in darkness, then filtered through diatomaceous earth rinsing twice with chloroform. To the combined red-orange diazoethane filtrate is added a solution of the ionophore A-23187 (one molar equivalent, based on hydrazone) in chloroform. After stirring overnight, the color of the reaction solution is pale yellow and TLC analysis shows no remaining free A-23187. The reaction solution is diluted with chloroform, and glacial acetic acid (5 drops) is added to quench any remaining diazoalkane. Concentration under vacuum gives a pale yellow oil, which is purified by flash chromatography on silica gel using 5% methanol/chloroform as eluant. Compound 4 is obtained as a pale yellow microcrystalline solid.

Example 5

Preparation of A-23187, 1-(4,5-dimethoxy-2-nitrophenyl)ethyl ester (Compound 5)

A colorless solution of A-23187 in benzene is treated with one molar equivalent of 4,5-dimethoxy-2-nitrobenzyl bromide and 1.1 equivalents of 1,8-diazabicyclo[5.4.0]undec-7-ene (DBU). The resulting blue solution is heated until all starting ionophore is gone, as judged by TLC. The DBU.HBr side product is filtered off, and the filtrate concentrated under vacuum. Pure Compound 5 is obtained by flash chromatography as a pale yellow solid.

Example 6

Preparation of A-23187, desyl ester (Compound 6)

A colorless solution of A-23187 in benzene is treated with one molar equivalent of desyl bromide and 1.1 equivalents of 1,8-diazabicyclo[5.4.0]undec-7-ene (DBU). The resulting blue solution is heated at reflux temperature until all starting ionophore is gone, as judged by TLC. The DBU.HBr side product is filtered off, and the filtrate concentrated under vacuum. Pure Compound 6 is obtained pure by flash chromatography as a colorless solid.

Example 7

Preparation of A-23187, 2-methoxy-5-nitrophenol ester (Compound 7)

A colorless solution of A-23187 in dichloromethane is treated with one molar equivalent of 2-methoxy-5-nitrophenol, a catalytic amount of N-hydroxybenzotriazole, a catalytic amount of 4-dimethylaminopyridine, and 1.2 equivalents of EDAC. After stirring overnight, the reaction solution is washed with water, aqueous sodium bicarbonate, aqueous citric acid, and brine. The resulting solution is dried over anhydrous sodium sulfate and concentrated under vacuum. Pure Compound 7 is obtained by flash chromatography as a pale yellow solid.

Example 8

Preparation of A-23187, α-carboxy-2-nitrobenzyl ester (Compound 8)

A colorless solution of A-23187 in benzene is treated with one molar equivalent of t-butyl 2-bromo-2-(2-nitrophenyl) acetate and 1.1 equivalents of 1,8-diazabicyclo[5.4.0]undec-7-ene (DBU). The resulting blue solution is heated until all starting ionophore is gone, as judged by TLC. The DBU.HBr side product is filtered off, and the filtrate concentrated under vacuum. The intermediate product is purified by flash chromatography, yielding a colorless oil. Compound 8 is obtained by treating a solution of the intermediate in dichloromethane with ten molar equivalents of trifluoroacetic acid. When the reaction is judged complete by TLC, the volatiles are removed under vacuum and the residue purified by normal phase chromatography using chloroform/methanol/acetic acid to give Compound 8 as a pale yellow solid.

Example 9

The release of free ionophore in the vicinity of live cells upon photolysis

Figure 2:
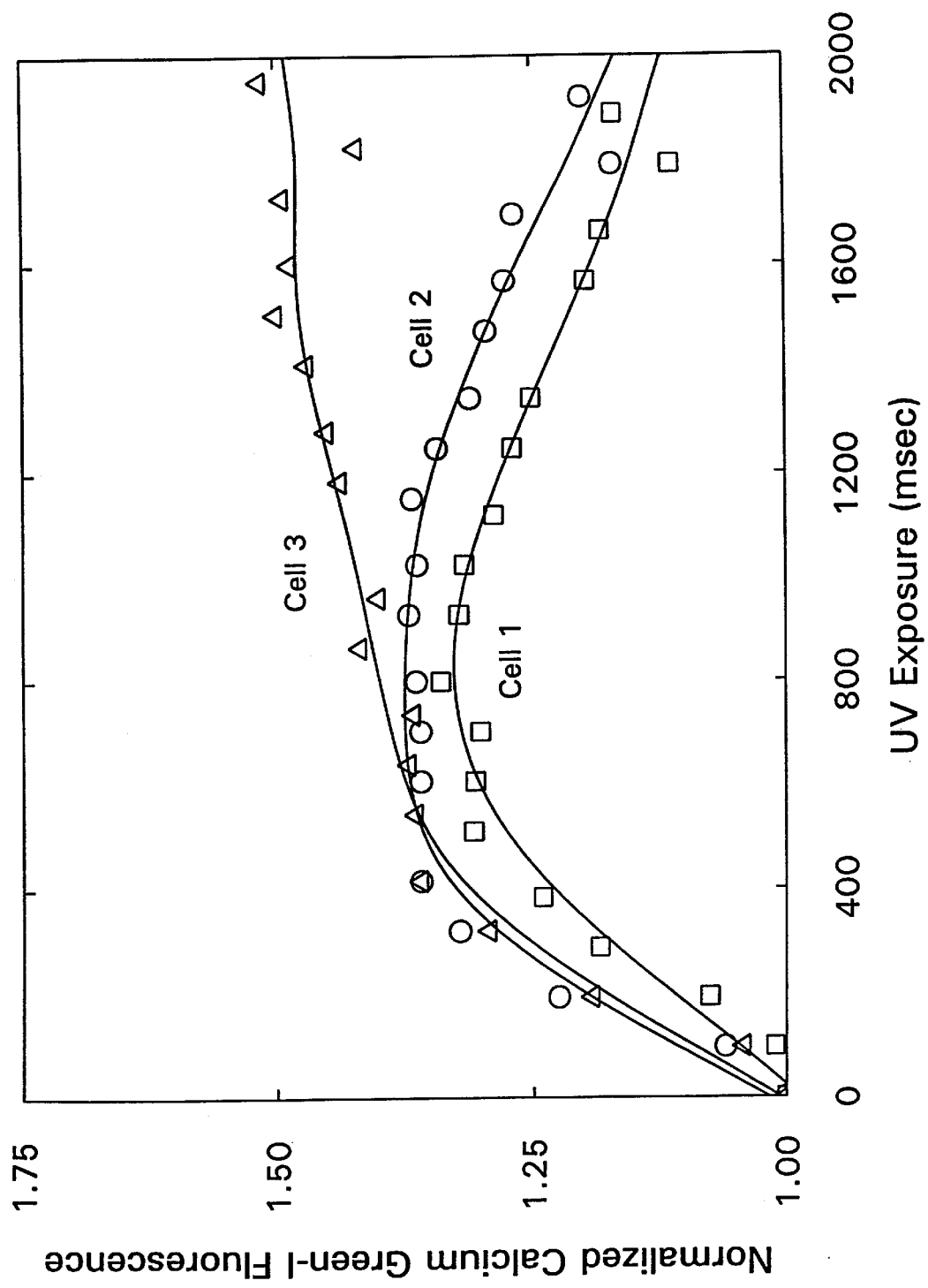
FIG. 2. Normalized fluorescence of CALCIUM GREEN-1 indicator in three individual 3T3 cells during the course of exposure to UV light in the presence of 10 $\mu$M caged-4-Br-A-23187 (Compound 2), as described in Example 9.

Adherent 3T3 fibroblasts are seeded onto an 18 mm×18 mm No. 1.5 glass coverslip and allowed to grow to approximately 25% confluency. The coverslip with cells is then washed briefly with Modified Tyrode's solution (hereafter referred to as MT; 135 mM NaCl, 5 mM KCl, 1 mM $MgCl_2$, 1.8 mM $CaCl_2$, 10 mM Na-HEPES, 5.6 mM D-glucose, pH 7.4) with 0.1% added bovine serum albumin (MT-BSA). The cells are subsequently loaded for 30 minutes at 37°° C. with 1 μM CALCIUM GREEN-1 AM indicator (Molecular Probes, Inc., Eugene Oreg.) in MT-BSA. The coverslip is then rinsed several times with MT containing 0.05% gelatin (MT-G), mounted on the bottom of an acrylic chamber (with the cells facing upward) and flooded with MT-G at room temperature. The chamber is then placed on the stage of a Nikon Diaphot TMD inverted microscope and a solution of 10 μM Compound 1 or Compound 2 in MT-G is washed continuously over the cells for 10 minutes while the excess solution is removed by suction. The caged ionophore is photoactivated using the epi-illuminator of a Nikon Diaphot TMD inverted fluorescence microscope equipped with a 40X Fluor 1.4 NA objective lens (Nikon, Melville, N.Y.) and a dichroic mirror that reflects 340–485 nm light with high efficiency (Omega Optical, Brattleboro, Vt.)). A 10-position motorized filter wheel (Sutter Instrument Co.), fitted with interference filters centered at 365 nm and 485 nm, is used to alternate exposure of the cells between 365 nm light (for 100 msec periods) and 485 nm light (to acquire images of CALCIUM GREEN-1 indicator fluorescence). Increases in cytosolic free calcium in the 3T3 cells resulting from photoactivation of the ionophore are indicated by the enhanced 485 nm light-excited fluorescence of intracellular CALCIUM GREEN-1 indicator with increasing exposure of the cells to 365 nm light. FIG. 1 illustrates the normalized fluorescence of CALCIUM GREEN-I indicator in three individual 3T3 cells during the course of exposure to UV light in the presence of 10 μM caged-A23187. FIG. 2 illustrates the equivalent experimental results wherein 10 μM caged-Br-A23187 is substituted for caged-A23187.

Example 10

Increase in intracellular free calcium due to photolysis of caged ionophores in cells Adherent 3T3 fibroblasts are seeded onto an 18 mm×18 mm No. 1.5 glass coverslip and allowed to grow to approximately 25% confluency. The coverslip with cells is then washed briefly with Modified Tyrode's solution (MT; 135 mM NaCl, 5 mM KCl, 1 mM $MgCl_2$, 1.8 mM $CaCl_2$, 10 mM Na-HEPES, 5.6 mM D-glucose, pH 7.4) with 0.1% added bovine serum albumin (MT-BSA). The cells are subsequently loaded by immersion in 10 μM Fluo-3 AM (Molecular Probes, Inc., Eugene Oreg.) in MT-BSA for 30 minutes at 37° C. The coverslip is then rinsed gently several times with MT containing 0.05% gelatin (MT-G) and incubated with 50 μM of either Compound 1 or Compound 2 for 10 minutes at room temperature. The coverslip is then rinsed gently with excess MT-BSA, inverted over a drop of MT-BSA on a glass microscope slide, and the edges of the coverslip are sealed with melted paraffin. The chamber is placed on the stage of a Zeiss Axioplan upright fluorescence microscope. The caged ionophore is photoactivated using the epi-illuminator of a microscope equipped with a 40×0.75 NA objective lens (Carl Zeiss) and standard DAPI longpass and fluorescein longpass epi-fluorescence filter sets. The field diaphragm of the epi-illuminator is used to limit the area of the field of cells that is exposed to UV illumination. With the field diaphragm closed such that 3 or 4 cells are illuminated, the DAPI filter is moved into place and the cells are exposed to UV light by holding the shutter open for one second or greater. After UV exposure, the shutter is closed, the fluorescein filter set is moved into the light path and the epi-illuminator field diaphragm is opened to allow examination of the entire field. An increase in cytosolic free calcium in the 3T3 cells resulting from photoactivation of cell-associated caged ionophore is indicated by the enhanced 485 nm light-excited fluorescence of intracellular fluo-3 in cells exposed to TV light.

It is to be understood that, while the foregoing invention has been described in detail by way of illustration and example, numerous modifications, substitutions, and alterations are possible without departing from the spirit and scope of the invention as described in the following claims.

What is claimed is:

1. A caged ionophore that is an ester of a carboxylic acid that is present on a free ionophore selected from the group consisting of nigericin, ionomycin, A-23187, 4-Br-A-23187 and monensin, and that upon photolysis regenerates said nigericin, ionomycin, A-23187, 4-Br-A-23187 or monensin.

2. A caged ionophore, as claimed in claim 1, wherein said free ionophore is nigericin, A-23187 or 4-Br-A-23187.

3. A caged ionophore, as claimed in claim 2, wherein the ester of the carboxylic acid is selected from the group consisting of a nitrobenzyl ester having a nitrobenzyl portion, a desyl ester having a desyl portion, and a 2-alkoxy-5-nitrophenyl ester having a 2-alkoxy-5-nitrophenyl portion.

4. A caged ionophore, as claimed in claim 3, wherein said free ionophore is A-23187 or 4-Br-A-23187.

5. A caged ionophore, as claimed in claim 3, wherein the ester of the carboxylic acid is a nitrobenzyl ester.

6. A caged ionophore, as claimed in claim 5, wherein said nitrobenzyl portion of said nitrobenzyl ester has the formula:

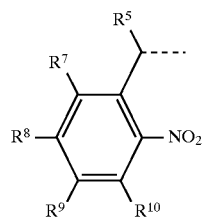

wherein $R^5$ is H, $CH_3$, or $CO_2R^6$, where $R^6$ is H, $C_1$–$C_6$ alkyl, an alpha-acyloxyalkyl ester having 3–6 carbons, an alkali metal, or $R^6$ is a succinimide, such that $CO_2R^6$ is a succinimidyl ester;

$R^7$ is H, alkoxy having 1–6 carbons, —$O(CH_2)_nCO_2R^{11}$ or $NO_2$;

$R^8$, $R^9$ and $R^{10}$ are independently H, $C_1$–$C_6$ alkoxy, or —$O(CH_2)_nCO_2R^{11}$;

or $R^8$ taken in combination with $R^9$ is —O—$CH_2$—O—;

wherein n=1–18 and $R^{11}$ is H, $C_1$–$C_6$ alkyl, or $R^{11}$ is a succinimide, such that $CO_2R^{11}$ is a succinimidyl ester.

7. A caged ionophore, as claimed in claim 6, wherein $R^5$ is $CH_3$ or $CO_2R^6$ where $R^6$ is H or an alkali metal, $R^8$ and $R^9$ are each H or —$OCH_3$, or $R^8$ taken in combination with $R^9$ is —O—$CH_2$—O—, $R^7$ is H or $NO_2$, and $R^{10}$ is H.

8. A caged ionophore, as claimed in claim 3, wherein the ester of the carboxylic acid is a desyl ester.

9. A caged ionophore, as claimed in claim 8, wherein the desyl portion of said desyl ester has the formula

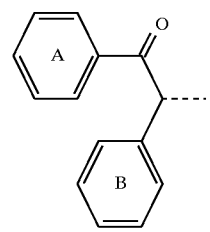

wherein aromatic rings A and B are optionally and independently substituted one or more times by H, halogen, —$NO_2$, —$OR^{13}$, and —$NR^{14}R^{15}$ where $R^{13}$, $R^{14}$ and $R^{15}$ are independently alkyl groups having 1–6 carbons.

10. A caged ionophore, as claimed in claim 3, wherein the ester of the carboxylic acid is a 2-alkoxy-5-nitrophenyl ester.

11. A caged ionophore, as claimed in claim 10, wherein the 2-alkoxy-5-nitrophenyl portion of said 2-alkoxy-5-nitrophenyl ester has the formula:

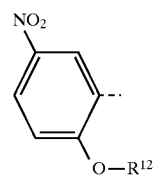

wherein $R^{12}$ is a $C_1$–$C_6$ alkyl.

12. A caged ionophore, as claimed in claim 1 having the formula

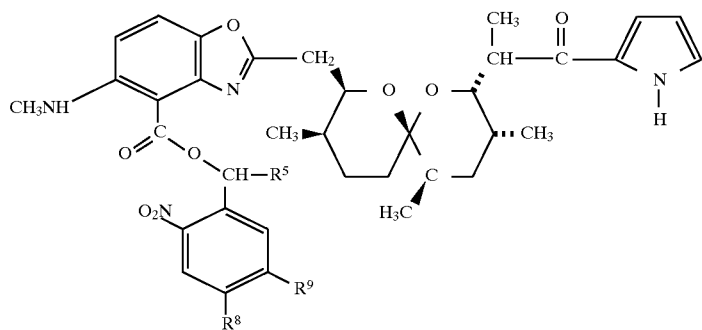

or the formula

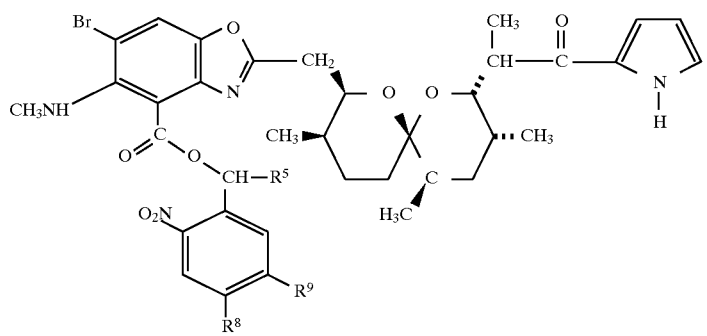

wherein $R^5$ is $CH_3$ or $CO_2R^6$ where $R^6$ is H or an alkali metal, $R^8$ and $R^9$ are independently H or —$OCH_3$, or $R^8$ taken in combination with $R^9$ is —O—$CH_2$—O—.

13. A method of modulating an ion concentration across a membrane separating unequal ion concentrations, comprising:
   a) adding to the membrane a caged ionophore that is an ester of a carboxylic acid that is present on a free ionophore selected from the group consisting of nigericin, ionomycin, A-23187, 4-Br-A-23187 or monensin;
   b) illuminating the membrane at a site where ion transport is desired, with a wavelength selected to release the free ionophore and change the unequal ion concentrations across said membrane.

14. A method, as claimed in claim 13, wherein the membrane is illuminated at a wavelength of 300–400 nm.

15. A method, as claimed in claim 13, wherein the unequal ion concentrations are concentrations of ions selected from the group consisting of $H^+$, $Na^+$, $K^+$, $Ca^{2+}$, $Mn^{2+}$, $Mg^{2+}$ and $Zn^{2+}$.

16. A method, as claimed in claim 13, wherein the membrane separating the unequal ion concentrations comprises an artificial membrane.

17. A method, as claimed in claim 13, wherein the caged ionophore is an ester of a carboxylic acid is selected from the group consisting of a nitrobenzyl ester having a nitrobenzyl portion, a desyl ester having a desyl portion, or a 2-alkoxy-5-nitrophenyl ester having a 2-alkoxy-5-nitrophenyl portion.

18. A method, as claimed in claim 13, wherein said free ionophore is nigericin, A-23187 or 4-Br-A-23187.

19. A method, as claimed in claim 13, wherein the caged ionophore added to the membrane is an ester of a carboxylic acid on an ionophore that is A-23187, where said caged ionophore is essentially non-fluorescent until illuminated at the wavelength selected to release the ionophore.

20. A method, as claimed in claim 19, wherein the caged ionophore has the formula

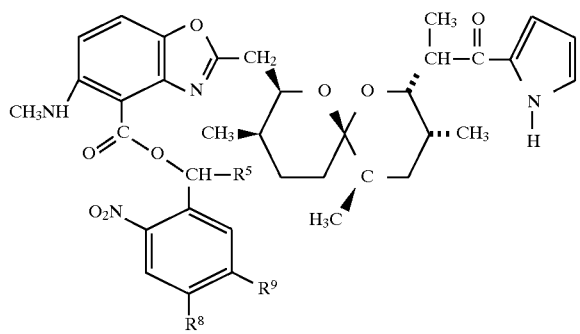

wherein $R^5$ is $CH_3$ or $CO_2R^6$ where $R^6$ is H or an alkali metal, $R^8$ and $R^9$ are each H or —$OCH_3$, or $R^8$ taken in combination with $R^9$ is —O—$CH_2$—O—.

* * * * *

UNITED STATES PATENT AND TRADEMARK OFFICE
CERTIFICATE OF CORRECTION

PATENT NO. : 5,888,829
DATED : March 30, 1999
INVENTOR(S) : Gee et al.

It is certified that error appears in the above-identified patent and that said Letters Patent is hereby corrected as shown below:

Column 3,
Line 37, "$Mg^{2+}>Ba^{2+}$" should read -- $Mg^{2+}>SR^{2+}>Ba^{2+}$ --.

Column 8,
Line 60, "calorimetric" should read -- colorimetric --.
Line 67, "calorimetric" should read -- colorimetric --.

Column 13,
Line 23, "TV" should read -- UV --.

Column 15,
Line 44, "or" should read -- and --.

Signed and Sealed this

Seventeenth Day of September, 2002

Attest:

JAMES E. ROGAN
*Attesting Officer*     *Director of the United States Patent and Trademark Office*